United States Patent
Huang et al.

(10) Patent No.: US 9,988,669 B2
(45) Date of Patent: Jun. 5, 2018

(54) MEDIUM USED FOR BLOOD SAMPLE COLLECTION AND TRANSPORT

(71) Applicant: Abbott Molecular Inc., Des Plaines, IL (US)

(72) Inventors: Shihai X. Huang, Lincolnshire, IL (US); Laurence Phillips, Traisen (DE); Phillip Lefebvre, Lincolnshire, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 38 days.

(21) Appl. No.: 14/681,760

(22) Filed: Apr. 8, 2015

(65) Prior Publication Data

US 2015/0292993 A1  Oct. 15, 2015

Related U.S. Application Data

(60) Provisional application No. 61/962,319, filed on Apr. 14, 2014.

(51) Int. Cl.
| | | |
|---|---|---|
| *G01N 1/38* | (2006.01) | |
| *C12Q 1/68* | (2018.01) | |
| *G01N 33/487* | (2006.01) | |
| *B01L 3/00* | (2006.01) | |
| *G01N 1/28* | (2006.01) | |

(52) U.S. Cl.
CPC .......... *C12Q 1/6806* (2013.01); *B01L 3/5023* (2013.01); *G01N 33/487* (2013.01); *B01L 2200/16* (2013.01); *B01L 2400/0677* (2013.01); *G01N 1/28* (2013.01)

(58) Field of Classification Search
None
See application file for complete search history.

(56) References Cited

U.S. PATENT DOCUMENTS

| | | |
|---|---|---|
| 5,342,627 A | 8/1994 | Chopra et al. |
| 5,762,961 A | 6/1998 | Roser et al. |
| 6,716,392 B1 | 4/2004 | Putcha et al. |
| 7,638,099 B2 | 12/2009 | Lloyd et al. |
| 2004/0132207 A1 | 7/2004 | Arima et al. |
| 2006/0057554 A1 | 3/2006 | Watling et al. |
| 2006/0099567 A1 | 5/2006 | Muller-Cohn et al. |
| 2008/0307117 A1 | 12/2008 | Muller-Cohn et al. |
| 2009/0246750 A1 | 10/2009 | Lloyd et al. |
| 2010/0209927 A1 | 8/2010 | Menon et al. |
| 2011/0104271 A1 | 5/2011 | Thoorens et al. |
| 2011/0136771 A1 | 6/2011 | Ahmed et al. |
| 2013/0090253 A1 | 4/2013 | Dixon et al. |
| 2013/0253009 A1 | 9/2013 | Maggio |
| 2013/0280725 A1 | 10/2013 | Ismagilov et al. |

FOREIGN PATENT DOCUMENTS

WO    2013122754 A1    8/2013

*Primary Examiner* — Antonio Galisteo Gonzalez
(74) *Attorney, Agent, or Firm* — Pierce Atwood LLP; Kevin M. Farrell; David J. Wilson

(57) ABSTRACT

The present invention provides materials and methods for the stable transport of aqueous biological samples without refrigeration. Samples stabilized and handled by the methods of the present invention are stable for weeks, months or longer.

13 Claims, No Drawings

MEDIUM USED FOR BLOOD SAMPLE COLLECTION AND TRANSPORT

BACKGROUND

Blood samples are critical to the detection, diagnosis and progression of diseases and the treatment of many diseases. Pathogens, toxins (e.g., those produced by pathogens) and bodily defense molecules (e.g., antibodies, cytokines, etc) can be detected and monitored for a variety of disease states and treatment progression by analysis of, for example, a subject's blood sample.

Such analyses may include, for example, immunological, genetic and pathogenic analyses. In underdeveloped areas of the world it is often necessary to obtain a blood sample from a subject and transport it to a distant laboratory facility for processing and analysis. In other instances, samples may be delayed or may need to be stored for extended periods of time prior to testing. In order to obtain accurate results the sample must be stably maintained until analysis. Further, complete or near complete recovery of the sample is often critical to ensure accurate results.

Dried blood spot (DBS) testing is a well-known methodology for collecting and stabilizing a blood sample for later analysis. In this method, a blood sample is absorbed into a substrate (commonly filter paper such as Whatman 903®), and dried. For example, in the prior art, the blood may be held within the fibers or on the substrate. Other fibrous materials may also be used as substrates for DBS testing such as cellulose acetate fibers, cellulose, nitrocellulose, carboxymethylcellulose, hydrophilic polymers, polypropylene, polyester, polyamide, carbohydrate polymers, polytetrafluroethylene, cotton, fiberglass and combinations thereof. See, U.S. Pat. No. 7,638,099 to Lloyd, et al. In each case, the substrate is inert so as not to interfere with the intended assay.

In order to analyze a dried blood spot, extraction or solubilization from the filter paper (or other substrate) is required. For that purpose the filter paper, or a portion (usually a disc), is cut out of the filter paper and is placed into a container. The extraction procedure is then carried out using an appropriate solvent. After extraction and centrifugation, the supernatant is collected and analyzed.

The conventional DBS method described briefly above, by its very nature, results in extended processing time because of the need to resolubilize the sample from the substrate. Further, loss of sample or sample components may occur because of retention on the filter paper. Further still, portions of the filter paper (e.g., paper punches) selected for resolubilization may not provide for an even representation of the distribution of sample across the filter paper. These problems with the present technology introduce significant variability and bias into assay results. U.S. Patent Application No. 2013/0090253 to Dixon, et al.

Prior art methods of correcting for these problems are either complicated or ineffective. U.S. Patent Application No. 2013/0090253 to Dixon, et al., proposed a method of excising a sector-shaped (wedge) sample from a DBS instead of a circular paper punch stating that the sector-shaped sample would provide for a more accurate sample distribution. However, this method does not solve the problem of sample retention.

U.S. Pat. No. 7,638,099 and U.S. Patent Application No. 2009/0246750, both to Lloyd, et al., are directed towards a complicated container for the collection and air-drying of bodily fluid samples, said device comprising a matrix made of absorbent materials such as cellulose acetate fibers, cotton, etc. The container of Lloyd, et al., is expensive to manufacture and does not solve the problems recognized herein with regard to sample retention.

U.S. Patent Application No. 2004/0132207 to Arima, et al., discloses a method of stabilizing a blood sample by collecting it in pH buffered reagents and storing the sample in a buffer with a mildly weak acidic pH in the range of pH 7.0 to 8.0. The method requires fluid reagents, dedicated collection devices and does not provide for dry storage and transport of a blood sample.

U.S. Patent Application No. 2006/0057554 to Watling, et al., discloses a sample collection device for a fluid sample comprising an inert (non-dissolvable) absorbing matrix. Watling discloses that the absorbent material may be in the shape and size of a small tablet and, thus, frequently refers to the inert absorbing matrix as a tablet. See, Watling ¶¶ [0017], [0023] and [0029]. However, since the matrix of Watling is inert and non-dissolvable Watling does not solve the retention problems of the prior art.

U.S. Patent Application No. 2013/0280725 to Ismagilov, et al., discloses a complicated microfluidic device for preservation and storage of fluid biospecimens, the device comprising a membrane and/or desiccant.

What is needed are new materials and methods that provide for the increased efficiency and accuracy of blood sample acquisition and processing in a cost effective manner.

SUMMARY OF THE INVENTION

The present invention is directed towards new methods and materials for the collection, transport and solubilization of blood samples for further testing. Samples may be obtained directly from subjects or from previously collected blood. Further, the materials and methods of the present invention can be used for the collection, transport and solubilization of other bodily fluids such as, but not limited to, tears, sweat, saliva, semen, plasma, serum, lymph fluid, amniotic fluid, urine, mucus, etc.

In the present invention, a bodily fluid, for example blood, is collected from a subject or collection device and applied to the surface of a tablet. Application and drying of the sample allows the sample to be sorbed (i.e., sorption) by the tablet by adherence to the tablet surface (adsorbed) and/or permeate the tablet (absorbed at least partially) and thereby stabilizes the sample for storage and transport. If the sample is adsorbed and/or absorbed depends upon the nature of the sample and composition of the tablet. The tablet may be comprised of, for example, one or more salts, one or more stabilizers, one or more binders, one or more absorptive agents, one or more reactive agents, etc. The blood (or other bodily fluid) is dried either by air drying or by applied heat (i.e., about 70-110° F.) and/or air movement (i.e., a blower to move ambient air). Once dried onto and/or into the tablet the sample is stable and transport is easily accomplished. No refrigeration is needed and the dried/stabilized samples are stable for several weeks, several months or more. Transport of dried/stabilized samples can be performed with any available transportation means so long as the samples are kept clean and dry. Preparation would include the labeling and packaging of the samples in containers made for or suitable for such use.

Once the tablet with the applied sample is delivered to the facility that will perform analysis, the tablet, comprising the sample, is dissolved in an appropriate volume of an appropriate solution. For example, distilled water is suitable for samples that have been collected on tablets comprising the constituents of a buffered saline solution. In another example, the tablet may be dissolved into a buffered saline solution if, for example, the tablet does not comprise constituents of a buffered saline solution. One of ordinary skill in the art will be able to determine the composition of a tablet needed based on the nature of the sample to be collected and the assay to be performed, in view of the teachings of this specification. In some instances, for example if the tablet composition is inappropriate for a given assay, adsorbed samples may be scraped off the tablet surface and manipulated as desired. With the compositions and methods of the present invention recovery of the sample is typically above 99%, above 99.5%, above 99.9% and usually 100%.

The present invention contemplates a method for stabilizing an aqueous biological sample to be used for analysis, the method comprising depositing a quantity of the aqueous biological sample onto the surface of a dissolvable tablet and allowing the sample to dry and be sorbed by the dissolvable tablet creating a stabilized sample. The present invention further contemplates that the aqueous biological sample comprises one or more samples selected from the group consisting of blood, tears, sweat, saliva, semen, plasma, serum, lymph fluid, amniotic fluid, urine and mucus.

The present invention contemplates that the dissolvable tablet comprises the ingredients for a buffered saline solution. The present invention further contemplates that the dissolvable tablet comprises one or more excipients selected from a group consisting of diluents, binders, absorbents, hardeners, lubricants, glidants, disintegrants, gelling agents, and coloring agents.

The present invention further contemplates that the sample size is about 25 µl to about 400 µl; about 100 µl to about 250 µl; and about 100 µl or about 200 µl.

The present invention contemplates that the dissolvable tablet is essentially disk shaped and said disk has at least one concave surface. The present invention further contemplates that the dissolvable tablet comprises a coating. The present invention further contemplates that the aqueous biological sample is partly absorbed into the dissolvable tablet.

The present invention contemplates a method of using the stabilized sample of the present invention, the method comprising dissolving the dissolvable tablet comprising the sorbed stabilized sample into an aqueous solution to create a dissolved sample prior to performing one or more assays on the sample. The present invention further contemplates that the recovery of the sample is greater than 95%, greater than 99% and up to about 100%.

The present invention contemplates that the dissolvable tablet of the present invention further comprises one or more reagents specific for a defined biological assay. The present invention further contemplates that the defined biological assay is polymerase chain reaction. The present invention further contemplates that the dissolvable tablet further comprises one or more lysis reagents.

The present invention contemplates a method for stabilizing an aqueous biological sample for subsequent analysis, and for providing an incubation mixture for subsequent analysis, the method comprising: a) providing a dissolvable tablet, the dissolvable tablet comprising buffer salts; b) contacting the dissolvable tablet with an aqueous biological sample under conditions appropriate for sorption of the aqueous biological sample to the dissolvable tablet thereby forming a sorbed biological sample; c) drying the sorbed biological sample; and d) dissolving the dissolvable tablet and the sorbed biological sample to generate a buffered aqueous solution containing resolubilized biological sample.

The present invention contemplates a dissolvable tablet comprising the ingredients for a buffered saline solution and a dried blood sample of between 25 µl to 400 µl, wherein the tablet is between 95-100% soluble. The present invention further contemplates that the tablet is between 98%-100% soluble. The present invention further contemplates that the blood sample is between 100 µl to about 250 µl. The present invention further contemplates that the tablet further comprises potassium chloride.

DETAILED DESCRIPTION OF THE INVENTION

Definitions

The term "tablet," as used herein, shall refer to solid particles containing or including compounds that are compressed (with or without heat) under pressure to any desired shape and size, such as a pill, pellet, puck or caplet. Further, tablets may be shaped from a soft mass and allowed to dry with or without the use of pressure. Exemplary compounds suitable for use in the tablets of the present invention are discussed elsewhere in this specification. The tablets of the present invention feel dry to the touch.

The term "tablet" may also refer to "pellets, "pucks" or other shapes. In this regard, the shape of the "tablet" is not important. Rather, the tablet must be able to retain its integrity when exposed to the sample but must also be dissolvable when placed into a suitable volume of liquid. To put it another way, the tablet must have suitable mass to allow for the sample to be sorbed by the tablet while retaining its integrity but must be dissolvable when exposed to a suitable quantity of liquid. The tablet may be made by conventional means, as is discussed below, or may be made by lyophilization, so long as the tablet has the characteristics discussed above with regard to sorptive qualities and dissolvability qualities. With regard to the phrase "retain its integrity," it is contemplated that this term allows that the tablet may dissolve to a limited degree at the point of application of the sample until the sample dries.

The "tablet" may be placed in a small collection tube or similar container such that the sample is applied to the tablet while the tablet is in the collection tube. After drying, the sample is stable and the tube can be closed or sealed until further processing is performed. Also, the "tablet" may be placed in a collection tube after application of the sample and before or after the drying of the sample.

The term "excipient," as used herein, shall refer to non-therapeutic and/or non-active ingredients in a tablet that provide for preferred physical or aesthetic qualities. Tablets generally are formulated with desired levels of hardness, disintegration, dissolution rate, friability (i.e., ability to break down upon contact with, for example, an aqueous solution), stability and size. In the present invention color may facilitate effective observation of an applied sample to ensure that sufficient sample volume is applied. Color may also facilitate the observation of sample drying. Further, color may be used for easy identification of tablets of different compositions or uses. Specific types of excipients commonly used in tablet composition which may be used with the present invention include, for example, diluents, binders, absorbents, hardeners, lubricants, glidants, disntegrants, gelling agents, and coloring agents. Many of these excipients are used because the active ingredients alone may have poor compactablity and/or adhesion qualities and, thus, the excipients are needed to achieve the desired tableting goals. One excipient may provide one or more of the above listed functions. For example, a binding agent may also provide absorbency or hardness.

The terms "active (when the context makes it clear that the term is being used with regard to a tablet ingredient)," "active agent," "active compound" or "active ingredient," shall be synonymous herein and, as used herein, shall refer to compounds that perform a desired function. An active ingredient may provide for a buffered saline solution (or other desired solution) upon dissolution of the tablet. An active ingredient may also provide desired assay reagents upon dissolution of the tablet.

The terms "stabilize," "stabilizing," "stabilized" or similar (e.g., secure, fix, process, prepare, affix, obtain, sequester), as used herein, refer to the act of drying the sample onto (and/or into) the tablet. In this context, stabilize means that the sample is applied to the tablet in such a way that it will not be readily released by normal handling procedures used in the transport and laboratory manipulation of the tablet stabilized sample until it is deposited into a solution such as an aqueous solution.

The terms "dissolve," "dissolvable" and "dissolvability" as used herein, refer to mixing the tablet with a liquid such that the tablet's integrity is disrupted and the tablet's constituents and the sample to pass into solution. The solution may change in viscosity after the dissolvable tablet is dissolved into a liquid. The liquid may be aqueous or may be non-aqueous. The dissolvable tablet may dissolve fully or completely or may dissolve partially. "Partially dissolved" means that at least some of tablet's constituents and the sample to pass into solution, but that certain components of the tablet are not miscible in the liquid into which the tablet has been dissolved. Certain absorbents such as discussed elsewhere in this specification are examples of constituents of a tablet of the present invention that may not dissolve.

Tablet Manufacture

The manufacture of tablets is well known in the art.

In the tablet-pressing process, it is important that all ingredients be fairly dry, powdered or granular, somewhat uniform in particle size, and freely flowing. Mixed particle sized powders segregate during manufacturing operations due to different densities, which can result in tablets with poor content uniformity but use of uniform sized ingredients should prevent this. Content uniformity ensures that each tablet possesses the desired characteristics. Some tablets may be comprised of pure active agents but commonly excipients are included. Normally, a pharmacologically inactive or inert ingredient (an excipient) termed a binder is added to help hold the tablet together and give it strength. A wide variety of binders may be used. Some common binders include lactose, dibasic calcium phosphate, sucrose, corn (maize) starch, microcrystalline cellulose, povidone polyvinylpyrrolidone and modified cellulose (for example hydroxypropyl methylcellulose and hydroxyethylcellulose). Often, an ingredient is also included to act as a disintegrant to aid tablet dispersion once delivered to an aqueous solution thereby releasing the constituents. Some binders, such as starch and cellulose, are also excellent disintegrants.

Tablets can be made in virtually any shape. A shape useful in the present invention is a disk shape with a concave surface on at least one of the disk faces for sample placement.

Tablet diameter and shape are determined by end use as well as by the machine tooling used to produce them. The thickness of the tablet is determined by the amount of tablet material and the position of the punches in relation to each other during compression. Tablets should to be hard enough that they do not break up in storage, transport and use, yet friable enough that they disintegrate in a liquid.

The hardness of tablets is the principle measure of mechanical strength. Hardness is tested using a tablet hardness tester, as is known in the art. The units for hardness are commonly measured in kilograms per square centimeter. Models of tester known in the art include the Monsanto (or Stokes) Hardness Tester from 1930, the Pfizer Hardness Tester from 1950, the Strong Cob Hardness Tester and the Heberlain (or Schleeniger) Hardness Tester.

Lubricants prevent ingredients from clumping together and from sticking to the machinery. Lubricants also ensure uniform filing of the die and ensure ejection can occur with low friction between the tablet and die wall. Common minerals like talc or silica, and fats, e.g., vegetable stearin, magnesium stearate or stearic acid are the most frequently used lubricants in tablets.

Manufacture of the tabletinq blend. In the tablet pressing process, the main guideline is to ensure that each tablet contains the appropriate amount of active and inactive ingredient(s). Hence, all the ingredients should be well-mixed. If a sufficiently homogenous mix of the components cannot be obtained with simple blending processes, the ingredients must be granulated prior to compression to assure an even distribution of the active compound in the final tablet. Two basic techniques are known in the art to granulate powders for compression into a tablet: wet granulation and dry granulation. Powders that can be mixed well do not require granulation and can be compressed into tablets through direct compression.

Wet granulation. Wet granulation is a process of using a liquid binder to lightly agglomerate the powder mixture. The amount of liquid has to be properly controlled, as over-wetting will cause the granules to be too hard and under-wetting will cause them to be too soft and friable. Aqueous solutions have the advantage of being safer to deal with than solvent-based systems but may not be suitable for drugs which are degraded by hydrolysis. The active ingredient and excipients are weighed and mixed. The wet granulate is prepared by adding the liquid binder/adhesive to the powder blend and mixing thoroughly. Examples of binders/adhesives include aqueous preparations of cornstarch, natural gums such as acacia, cellulose derivatives such as methyl cellulose, gelatin, and povidone. The damp mass is screened through a mesh to form pellets or granules. A conventional tray-dryer or fluid-bed dryer is then used to dry the granulation. After the granules are dried, they are passed through a screen to isolate granules of uniform size.

Low shear wet granulation processes use very simple mixing equipment and can take a considerable time to achieve a uniformly mixed state. High shear wet granulation processes use equipment that mixes the powder and liquid at a very fast rate and, thus, speeds up the manufacturing process. Fluid bed granulation is a multiple-step wet granulation process performed in the same vessel to pre-heat, granulate and dry the powders. It is used because it allows close control of the granulation process.

Dry granulation. Dry granulation processes creates granules by light compaction of the powder blend under low pressures. The compacts are then broken up gently to produce granules (agglomerates). This process is often used when the product to be granulated is sensitive to moisture and heat. Dry granulation requires active agents or excipients with cohesive properties and a 'dry binder' may need to be added to the formulation to facilitate the formation of granules.

Granule lubrication. After granulation, a final lubrication step is sometimes required to ensure that the tableting blend does not stick to the equipment during the tableting process. This usually involves low shear blending of the granules with a powdered lubricant, such as magnesium stearate or stearic acid.

Manufacture of the tablets. Whatever process is used to make the tableting blend, the process of making a tablet by powder compaction is very similar. First, the powder is filled into the die. After die filling, the upper punch is lowered into the die and the powder is uniaxially compressed to a desired porosity. Finally, the upper punch is pulled up and out of the die (decompression) and the tablet is ejected from the die.

Tablets of the present invention. In the present invention the formulation of the tablet takes into account the ability of the tablet to maintain its integrity upon application of and sorption of the aqueous sample to the tablet. In other words, the tablets of the present invention need to retain shape and not dissolve upon application of the sample but need to be dissolvable in aqueous solution to conduct the desired assay. One way to achieve this goal is to formulate the tablet to sorb small (approximately 50-400, approximately 100-350, approximately 150-300, approximately 175-250, approximately 190-225, approximately 200 µl) volumes of sample without dissolving or disintegrating but to be readily dissolvable upon immersion into an aqueous solution. The addition of an absorptive excipient to the tablet may facilitate this result. Another method of achieving this goal is to coat the tablets with moisture resistant coating. The sample (approximately 50-400, approximately 100-350, approximately 150-300, approximately 175-250, approximately 190-225, approximately 200 µl or approximately 100 µl) is then dried on and adheres (adsorbed) to the surface of the tablet; however, the tablet will readily dissolve upon immersion of the tablet into an aqueous or non-aqueous solution (depending on tablet constituents). Appropriate coating techniques are known in the art. Exemplary tablet formulations are given below. Others will be known to those of ordinary skill in the art.

In the present example the tablet may be disk shaped or essentially disk shaped and the disk may have at least one flat surface or at least one concave (bowl shaped) surface to aid in the retention of the sample on the tablet prior to the sample drying. The drying of the sample may be aided by applying low level heat or warmth to the sample by, for example, exposure to the sun, placement near a heat source (e.g., a heater), and/or application of warmth or heat by, for example a hair drier. Further, drying of the sample may be aided by exposure to a low humidity environment, for example, an air conditioned environment such as an air conditioned vehicle or a container comprising one or more desiccants; or exposure to moving air.

Sample Collection

Sample collection for the present invention is performed by methods known to those of ordinary skill in the art. For example, collection of blood may be by finger or heal prick. Sample collection of mucus, saliva, previously collected blood, collected urine, etc., can be by cotton swab or by pipette from a collected sample. Samples can be obtained from, for example, sample collection tubes or bags (e.g., tubes containing blood samples or blood bags). Further, samples can be obtained from previously frozen samples. In any event, samples are then dried onto a tablet of the present invention and stored or transported as necessary. The tablets comprising the sample, regardless of sample source, can be appropriately labeled and secured in suitable containers for transport and storage.

Samples may also be brushed onto the tablets of the present invention. For example, cervical screens usually include samples taken with brushes or similar implements. Said sample material can then be brushed or smeared onto the surface of a tablet of the present invention.

Infectious agents could be inactivated by application of the sample onto tablets of the present invention. Suitable tablets could be coated with and/or comprise, for example, antimicrobial agents. An exemplary use for this embodiment would be to inactivate mycobacteria in samples taken for detection of *Mycobacterium tuberculosis* (MTB). MTB is a pathogenic bacterial species in the genus *Mycobacterium*, the causative agent of tuberculosis (TB) and is highly infectious. Inactivating MTB prior to testing would help ensure the safety of technicians handling the samples.

Tablet Formulations

The present invention is not limited to specific tablet formulations. The following exemplary formulations, combined with the teachings of this specification, will allow one of ordinary skill in the art to formulate other tablet compositions for use with the present invention.

PBS (phosphate buffered saline): One 2000 mg tablet dissolved in 200 mL of deionized water yields 0.01 M phosphate buffer, 0.0027 M potassium chloride and 0.137 M sodium chloride, pH 7.4, at 25° C.

The following formulations are for wash and lysis solutions used in the Abbott m2000 platform, an automated detection and amplification system for nucleic acids. The formulas provided below for final concentrations for the recited reagents. These reagents can be formulated into a tablet by one of ordinary skill in the art, as discussed above. The volume of water required for dissolving the tablet to achieve the recited concentrations is dictated by the size of the tablet and the amount of reagents in the tablet.

mWash: 3.5 M GITC (guanidine isothiocynate); 5.0% Tween 20 (polysorbate 20); 50 mM KOAc (potassium acetate), pH 6.0.

mLysis: 4.66 GITC; 10% Tween 20; 100 mM Trizma™ [2-amino-2-(hydroxymethyl)-1,3-propanediol; tris(hydroxymethyl)aminomethane; tris base], pH 7.8

Other formulations are envisioned by the present invention. For example, the use of a lysis reagent(s) in the formulation of the tablet is desired in some embodiments to ensure lysis of cellular constituents of the sample upon dissolution of the tablet. For example, lysis of white blood cells in a blood sample may be required to ensure viral nucleic acids are available for detection in the desired assay. Also, reagents specific for a desired assay may be included in the tablet. For example, reagents suitable for processing PCR samples (e.g., nuclease inhibitors, guanidinium salts, guanidinium isothiocyanate (GITC), ionic detergent(s), etc.) may be included in the tablet.

In one embodiment, it is contemplated that the tablet is completely dissolved at room temperature in water or other aqueous solution or in a non-aqueous solution, depending on tablet composition. In other words it is completely soluble; it has complete solubility. Complete solubility is defined herein as being 99-100% dissolved at room temperature. It is also contemplated that the tablet is 98%, 95%, 90%, 85%, 80%, 75%, 60%, 50% or less soluble. In some embodiments it is contemplated that the tablet comprises mostly or only binders and/or sorptive agents. The tablet may also contain soluble reagents that may be inert in the subsequent assay. For example, the tablet may contain sugars, salts or soluble binding or crosslinking agents (e.g., starches, microcrystalline cellulose, polyvinyl pyrollidone and liquid glucose).

In one embodiment, the present invention contemplates a dissolvable tablet comprising the ingredients for a buffered saline solution and a dried blood sample, wherein the tablet has complete solubility. In another embodiment, the present invention contemplates a dissolvable tablet comprising the ingredients for a buffered saline solution and a dried blood sample, wherein the tablet is between 90-100% soluble. In another embodiment, the present invention contemplates a dissolvable tablet comprising the ingredients for a buffered saline solution and a dried blood sample, wherein the tablet is between 95-100% soluble. In another embodiment, the present invention contemplates a dissolvable tablet comprising the ingredients for a buffered saline solution and a dried blood sample, wherein the tablet is between 98-100% soluble. In another embodiment, the present invention contemplates a dissolvable tablet comprising the ingredients for a buffered saline solution and a dried blood sample of 25 μl to about 400 μl, wherein the tablet is between 95-100% soluble. In another embodiment, the present invention contemplates a dissolvable tablet comprising the ingredients for a buffered saline solution and a dried blood sample of 25 μl to about 400 μl, wherein the tablet is between 95-100% soluble and wherein said tablet further comprises a moisture resistant coating. In another embodiment, the present invention contemplates a dissolvable tablet comprising the ingredients for a buffered saline solution and a dried blood sample of 25 μl to about 400 μl, wherein the tablet is between 95-100% soluble and wherein said tablet wherein said tablet comprises sodium chloride. In another embodiment, the present invention contemplates a dissolvable tablet comprising the ingredients for a Tris-buffered saline solution and a dried blood sample of 25 μl to about 400 μl, wherein the tablet is between 95-100% soluble and wherein said tablet further comprises a moisture resistant coating. In another embodiment, the present invention contemplates a dissolvable tablet comprising the ingredients for a phosphate-buffered saline solution and a dried blood sample of 25 μl to about 400 μl, wherein the tablet is between 95-100% soluble and wherein said tablet further comprises a moisture resistant coating. In another embodiment, the present invention contemplates a dissolvable tablet comprising the ingredients for a phosphate-buffered saline solution and a dried blood sample of 25 μl to about 400 μl, wherein the tablet is between 95-100% soluble and wherein said tablet comprises potassium chloride. In another embodiment, the present invention contemplates a dissolvable tablet comprising the ingredients for a buffered saline solution and a dried blood sample of 100 μl to 250 μl, wherein the tablet is between 98-100% soluble and wherein said tablet further comprises potassium chloride. In another embodiment, the present invention contemplates a dissolvable tablet comprising the ingredients for a phosphate-buffered saline solution and a dried blood sample of 100 μl to 250 μl, wherein the tablet is between 98-100% soluble and wherein said tablet further comprises sodium chloride. In another embodiment, the present invention contemplates a dissolvable tablet comprising the ingredients for a phosphate-buffered saline solution and a dried blood sample of 25 μl to about 400 μl, wherein the tablet is between 95-100% soluble and wherein said tablet comprises sodium chloride. In another embodiment, the present invention contemplates a dissolvable tablet comprising the ingredients for a Tris-buffered saline solution and a dried blood sample of 25 μl to about 400 μl, wherein the tablet is between 95-100% soluble and wherein said tablet comprises sodium chloride.

Sample Assays

Samples will be assayed by standard assays known to those of ordinary skill in the art. For example, HIV testing can be performed by immunological assay or by detection of HIV specific genetic or proteinaceous material. Other viral infections (e.g., hepatitis) can be assayed by similar appropriate techniques. Other diseases that can be detected via blood samples are parasitic infections, immunological diseases (if the person has a detectable antibody titer), other medical conditions that can be detected by immunological testing (e.g., detection of prostate specific antigen), cholesterol levels, metabolic disorders (e.g., hypoparathyroidism, hyperparathyroidism, hypothyroidism, hyperthyroidism), blood sugar levels, diabetes, etc. In short, any condition that can be detected via blood can be detected by the sample handled by the methods of the present invention.

Likewise, standard testing of metabolic conditions and diseases that can be detected by analysis of non-blood bodily fluid samples can also be detected by use of the sample handled by the methods of the present invention. For example, many physiological conditions can be detected by testing of saliva. Lee and Wong, 2009, Am. J. Dent., 22(4): 241-248. Such conditions include disease causing agents such as, but not limited to, Human Immunodeficiency virus (HIV), Epstein-Barr virus (EBV), influenza, herpes, viral meningitis and Cytomegalovirus (CMV). Other diseases and physiological conditions, while not being transmitted through saliva, can be diagnosed via saliva. These include, for example, blood alcohol, substance abuse markers (e.g., cocaine metabolite, cocaine, cannabinoids, opiates), hormones (e.g., estradiol, progesterone, testosterone, DHEA, cortisol). Thus, saliva samples can be saved and processed by using the methods and compositions of the present invention for later testing for the detection of the aforementioned diseases and physiological conditions. One of skill in the art, by applying the teachings of this specification, will be able to develop appropriate tablet compositions for storage and transport of other bodily fluid samples without undue experimentation.

Further still, the tablets of the present invention can be used in the collection of cell samples for use in, for example, chromosome analysis. This may be accomplished, for example, by placing a porous collection apparatus (e.g., nylon mesh or filter paper) on a tablet of the present invention, applying the cell containing sample onto the collection apparatus and allowing the moisture from the sample to sorbe onto or into the tablet thereby collection the cells on the collection apparatus.

Method for Stabilizing an Aqueous Biological Sample

In some embodiments, the present invention contemplates a method for stabilizing an aqueous biological sample to be used for analysis, the method comprising depositing a quantity of the aqueous biological sample onto the surface of a dissolvable tablet and allowing the sample to dry and be sorbed by the dissolvable tablet creating a stabilized sample. In some embodiments of the above method, the method further comprises a tablet that is 30%-100% soluble. In some embodiments of the above method, the method further comprises a tablet that is 50%-100% soluble. In some embodiments of the above method, the method comprises a tablet that is 60%-100% soluble. In some embodiments of the above method, the method comprises a tablet that is 75%-100% soluble. In some embodiments of the above method, the method comprises a tablet that is 80%-100% soluble. In some embodiments of the above method, the method comprises a tablet that is 85%-100% soluble. In some embodiments of the above method, the method comprises a tablet that is 90%-100% soluble. In some embodiments of the above method, the method comprises a tablet that is 95%-100% soluble. In some embodiments of the above method, the method comprises a tablet that is 98%-100% soluble. In some embodiments of the above method, the method comprises a tablet that has complete solubility. In some embodiments of the above method, the present invention contemplates a method for stabilizing a blood sample to be used for analysis, the method comprising depositing a quantity of the aqueous biological sample onto the surface of a dissolvable tablet and allowing the sample to dry and be sorbed by the dissolvable tablet creating a stabilized sample, wherein the tablet has complete solubility. In some embodiments of the above method, the present invention contemplates a method for stabilizing a blood sample to be used for analysis, the method comprising depositing a quantity of the aqueous biological sample onto the surface of a dissolvable tablet and allowing the sample to dry and be sorbed by the dissolvable tablet creating a stabilized sample, wherein the tablet is between 95-100% soluble and wherein said tablet wherein said tablet comprises sodium chloride. In some embodiments of the above method, the present invention contemplates a method for stabilizing a blood sample to be used for analysis, the method comprising depositing a quantity of the aqueous biological sample onto the surface of a dissolvable tablet and allowing the sample to dry and be sorbed by the dissolvable tablet creating a stabilized sample, wherein the tablet is between 95-100% soluble and wherein said tablet wherein said tablet comprises a potassium salt. In some embodiments of the above method, the present invention contemplates a method for stabilizing a blood sample to be used for analysis, the method comprising depositing a quantity of the aqueous biological sample onto the surface of a dissolvable tablet and allowing the sample to dry and be sorbed by the dissolvable tablet creating a stabilized sample, wherein the tablet is between 95-100% soluble and wherein said tablet comprises the ingredients for a Tris-buffered saline solution. In some embodiments of the above method, the present invention contemplates a method for stabilizing a blood sample to be used for analysis, the method comprising depositing a quantity of the blood sample onto the surface of a dissolvable tablet and allowing the sample to dry and be sorbed by the dissolvable tablet creating a sorbed stabilized sample, wherein the tablet is between 90-100% soluble and wherein said tablet comprises the ingredients for a buffered saline solution, the method further comprising dissolving the dissolvable tablet comprising the sorbed stabilized sample into an aqueous solution to create a dissolved sample prior to performing one or more assays on the sample.

In some embodiments, the invention contemplates a method for stabilizing an aqueous biological sample for subsequent analysis, and for providing an incubation mixture for subsequent analysis, the method comprising:
a) providing a dissolvable tablet, the dissolvable tablet comprising buffer salts;
b) contacting the dissolvable tablet with an aqueous biological sample under conditions appropriate for sorption of the aqueous biological sample to the dissolvable tablet thereby forming a sorbed biological sample;
c) drying the sorbed biological sample; and
d) dissolving the dissolvable tablet and the sorbed biological sample to generate a buffered aqueous solution containing resolubilized biological sample.

In some embodiments of the above method, the buffer salts comprises sodium chloride. In some embodiments of the above method, the buffer salts comprises potassium chloride. In some embodiments of the above method, the tablet has complete solubility. In some embodiments of the above method, the tablet is 90%-100% soluble. In some embodiments of the above method, the tablet is 95%-100% soluble. In some embodiments of the above method, the tablet is 98-%-100% soluble. In some embodiments of the above method, the buffer salts comprises sodium chloride and is 95%-100% soluble. In some embodiments of the above method, the buffer salts comprises potassium chloride and is 95%-100% soluble. In some embodiments of the above method, the aqueous biological sample is blood, the buffer salts comprises sodium chloride and is 95%-100% soluble. In some embodiments of the above method, aqueous biological sample is blood, the buffer salts comprises potassium chloride and is 95%-100% soluble.

All ranges given herein are inclusive of all values within the given range. For example, the range of 99-100% includes all values from 99 to 100, inclusive. A range of "50% or less" includes all values from 50% to 0%, inclusive. Thus, for example, the values 99.3% or 45.2% find support in the present specification even though they are not specifically mentioned.

EXEMPLIFICATION

Example 1

This example was preformed to provide proof of concept support for the claimed invention.

Blood samples from finger pricks (200 µl) were deposited onto TBS (tris-buffered saline) tablets obtained from a standard supplier (Sigma-Aldrich). The blood dried in about 35 minutes. The tablets with dried blood dissolved completely in DI (distilled/deoxidized) water to create a blood suspension. Blood components were detected in the suspension via standard hemoglobin test strips.

Example 2

In this example blood samples obtained from persons with known viral infections (hepatitis) are used. The blood is dried onto TBS tablets as above. The tablets are dissolved as above and hepatitis RNA is detected by RT-PCR. Moyer, et al., 1999, Am. Fam. Physician, 1:59(1):79-88, 91-92. Appropriate nuclease inhibiting reagents and techniques are used. Control samples with non-infected blood test negative.

Example 3

In this example blood samples obtained from persons with known HIV infection are used. The blood is dried onto TBS tablets as above. The tablets are dissolved as above and HIV is detected in the solution via ELISA and elispot assay. Appropriate nuclease inhibiting reagents and techniques are used. Control samples with non-infected blood are negative.

Example 4

In this example saliva obtained from persons with unknown but suspected HIV infection are used. The saliva is dried onto TBS tablets as above or onto tablets comprising the lysis formulation above. The tablets are dissolved as above and presence of HIV is determined with a conventional HIV detection assay (such as an ELISA or elispot assay). As a control, a second sample from each person is tested directly using a conventional saliva assay. The results from samples dried to the tablets and the samples used in the conventional assay system are equivalent with samples that tested positive or negative in one assay also testing positive or negative in the other assay.

Example 5

In this example blood samples obtained from persons with known viral infections (hepatitis) are used. The blood is dried onto TBS tablets as above. The tablets with dried samples (stabilized samples) are placed in a clean, closed (although not necessarily air tight) container for a period of time before the tablets are dissolved and the assay performed. Appropriate nuclease inhibiting reagents and techniques are used. Tablets are assayed at one hour after drying, one day, one week, one month, three months, six months and one year after drying. No statistically significant reduction in detection of the target virus is seen throughout the course of the experiment.

What is claimed is:

1. A method for stabilizing an aqueous biological sample to be used for analysis, the method comprising depositing a quantity of the aqueous biological sample onto the surface of a dissolvable tablet and allowing the sample to dry and be sorbed by the dissolvable tablet, the dissolvable tablet essentially retaining its integrity, thereby creating a stabilized sample.

2. The method of claim 1, wherein the aqueous biological sample comprises one or more samples selected from the group consisting of blood, tears, sweat, saliva, semen, plasma, serum, lymph fluid, amniotic fluid, urine and mucus.

3. The method of claim 1, wherein said aqueous sample comprises blood.

4. The method of claim 1, wherein the dissolvable tablet comprises the ingredients for a buffered saline solution.

5. The method of claim 1, wherein the dissolvable tablet comprises one or more excipients selected from the group consisting of diluents, binders, absorbents, hardeners, lubricants, glidants, disintegrants, gelling agents, and coloring agents.

6. The method of claim 1, wherein the sample size is about 25 µl to about 400 µl.

7. The method of claim 6, wherein the sample size is about 100 µl to about 250 µl.

8. The method of claim 7, wherein the sample size is about 200 µl.

9. The method of claim 1, wherein said dissolvable tablet is disk shaped and said disk has at least one concave surface.

10. The method of claim 1, wherein the dissolvable tablet comprises a coating.

11. The method of claim 1, wherein the aqueous biological sample is partly absorbed into the tablet.

12. The method of claim 1, wherein the dissolvable tablet further comprises one or more lysis reagents.

13. The method of claim 1, wherein said tablet is at least 98% dissolvable.

* * * * *